United States Patent
Dai

(10) Patent No.: US 12,131,827 B2
(45) Date of Patent: Oct. 29, 2024

(54) KNOWLEDGE GRAPH-BASED QUESTION ANSWERING METHOD, COMPUTER DEVICE, AND MEDIUM

(71) Applicant: BOE TECHNOLOGY GROUP CO., LTD., Beijing (CN)

(72) Inventor: Yafei Dai, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 458 days.

(21) Appl. No.: 17/613,629

(22) PCT Filed: Feb. 8, 2021

(86) PCT No.: PCT/CN2021/076049
§ 371 (c)(1),
(2) Date: Nov. 23, 2021

(87) PCT Pub. No.: WO2021/164618
PCT Pub. Date: Aug. 26, 2021

(65) Prior Publication Data
US 2022/0254507 A1 Aug. 11, 2022

(30) Foreign Application Priority Data
Feb. 17, 2020 (CN) .......................... 202010096035.5

(51) Int. Cl.
*G16H 50/70* (2018.01)
*G06F 16/332* (2019.01)
(Continued)

(52) U.S. Cl.
CPC ......... *G16H 50/70* (2018.01); *G06F 16/3329* (2019.01); *G06F 40/242* (2020.01); *G06F 40/30* (2020.01); *G06N 5/02* (2013.01)

(58) Field of Classification Search
CPC .... G16H 50/70; G16H 10/20; G06F 16/3329; G06F 40/242; G06F 40/30; G06F 40/216;
(Continued)

(56) References Cited

U.S. PATENT DOCUMENTS

| 2016/0132648 A1* | 5/2016 | Shah | G16H 70/20 |
| | | | 705/2 |
| 2017/0109355 A1* | 4/2017 | Li | G06N 7/01 |

(Continued)

FOREIGN PATENT DOCUMENTS

| CN | 104035917 A | 9/2014 |
| CN | 106844603 A | 6/2017 |

(Continued)

OTHER PUBLICATIONS

Zhang Min; Teng Haibin; Jiang Ming; Wen Tao; Tang Jingfan. A Longest Matching Resource Mapping Algorithm with State Compression Dynamic programming Optimization. Intelligent Automation and Soft Computing 25.3: 625-635. Tech Science Press. (Sep. 2019) (Year: 2019).*

(Continued)

*Primary Examiner* — Linh Giang Le
(74) *Attorney, Agent, or Firm* — Lippes Mathias LLP

(57) ABSTRACT

Provided is a knowledge graph-based question answering method, including: receiving a query sentence; determining a target entity to which an entity mention in the query sentence is mapped in a knowledge graph; and outputting a result corresponding to the target entity in the knowledge graph.

16 Claims, 5 Drawing Sheets

(51) Int. Cl.
*G06F 40/242* (2020.01)
*G06F 40/30* (2020.01)
*G06N 5/02* (2023.01)

(58) Field of Classification Search
CPC .... G06F 40/247; G06F 40/284; G06F 40/295; G06F 16/367; G06N 5/02; G06N 3/042; G06N 5/04
See application file for complete search history.

(56) References Cited

U.S. PATENT DOCUMENTS

| | | | |
|---|---|---|---|
| 2019/0018839 | A1 | 1/2019 | Ge et al. |
| 2019/0317994 | A1* | 10/2019 | Singh .................. G06F 40/30 |

FOREIGN PATENT DOCUMENTS

| | | | |
|---|---|---|---|
| CN | 108681537 | A | 10/2018 |
| CN | 108804521 | A | 11/2018 |
| CN | 109657037 | A * | 4/2019 |
| CN | 110516260 | A | 11/2019 |
| CN | 111339267 | A | 6/2020 |

OTHER PUBLICATIONS

China National Intellectual Property Administration, First office action of Chinese application No. 202010096035.5 issued on Feb. 11, 2023, which is foreign counterpart application of this US application.
Extended European search report of counterpart European application No. 21756573.8 issued on Jul. 6, 2023.

* cited by examiner

KNOWLEDGE GRAPH-BASED QUESTION ANSWERING METHOD, COMPUTER DEVICE, AND MEDIUM

CROSS-REFERENCE TO RELATED APPLICATION

This application is a 371 of PCT Application PCT/CN2021/076049, filed Feb. 8, 2021, which claims the priority to Chinese Patent Application No. 202010096035.5, filed on Feb. 17, 2020, and entitled "KNOWLEDGE GRAPH-BASED QUESTION AND ANSWER METHOD AND SYSTEM, COMPUTER EQUIPMENT AND MEDIUM," the disclosures of which are herein incorporated by reference in their entireties.

TECHNICAL FIELD

The present disclosure relates to the field of computer technologies, and particularly relates to a knowledge graph-based question answering method and apparatus, a computer device, and a medium.

BACKGROUND

A conventional frequently asked questions (FAQ) question answering system needs to prepare question-answer (Q&A) pairs to answer questions based on the Q&A pairs. The Q&A pairs cover a narrow range, and it is difficult to match a question raised by a user against questions in the Q&A pairs. For example, it is very difficult to match the question "I feel dizzy and exhausted all the time. Do I have high blood pressure?" with "What are the typical symptoms of high blood pressure?" in an FAQ database. As a result, the FAQ question answering system has low accuracy.

SUMMARY

The present disclosure is intended to provide a knowledge graph-based question answering method and apparatus, a computer device, and a medium.

According to a first aspect of the present disclosure, a knowledge graph-based question answering method is provided. The method includes: receiving a query sentence; determining a target entity to which an entity mention in the query sentence is mapped in a knowledge graph; and outputting a result corresponding to the target entity in the knowledge graph.

In a possible implementation, determining the target entity to which the entity mention in the query sentence is mapped in the knowledge graph includes: extracting a semantic feature vector of the entity mention; and inputting the semantic feature vector of the entity mention into a preset neural network, such that the neural network matches the semantic feature vector of the entity mention against semantic feature vectors of entities in the knowledge graph and outputs a first matching result, wherein the first matching result is intended to indicate the target entity.

In a possible implementation, determining the target entity to which the entity mention in the query sentence is mapped in the knowledge graph includes: acquiring a second matching result by matching the entity mention against entities in the knowledge graph, wherein the second matching result includes a name of an entity matching the entity mention in the knowledge graph; and determining the entity indicated by the second matching result as the target entity.

In a possible implementation, determining the target entity to which the entity mention in the query sentence is mapped in the knowledge graph includes: matching the entity mention against entities in the knowledge graph; searching the entity mention in a name dictionary in response to an absence of a second matching result, wherein the name dictionary includes a standard name and at least one alternative name of each entity, a name of a same entity in the knowledge graph is the same as a corresponding standard name, and the second matching result includes a name of an entity matching the entity mention in the knowledge graph; and determining an entity corresponding to an alternative name containing the entity mention as the target entity in response to a presence of the alternative name containing the entity mention in the name dictionary.

In a possible implementation, determining the target entity to which the entity mention in the query sentence is mapped in the knowledge graph includes: matching the entity mention against entities in the knowledge graph; searching the entity mention in a name dictionary in response to an absence of a second matching result, wherein the name dictionary includes a standard name and at least one alternative name of each entity, a name of a same entity in the knowledge graph is the same as a corresponding standard name, and the second matching result includes a name of an entity matching the entity mention in the knowledge graph; and in response to an absence of an alternative name containing the entity mention in the name dictionary, extracting a semantic feature vector of the entity mention, and inputting the semantic feature vector of the entity mention into a preset neural network, such that the neural network matches the semantic feature vector of the entity mention against semantic feature vectors of entities in the knowledge graph and outputs a first matching result, wherein the first matching result is intended to indicate the target entity.

In some embodiments, inputting the semantic feature vector of the entity mention into the preset neural network, such that the neural network matches the semantic feature vector of the entity mention against the semantic feature vectors of the entities in the knowledge graph and outputs the first matching result includes: generating a candidate entity set based on feature comparison results between the entity mention and the entities in the knowledge graph; and inputting the semantic feature vector of the entity mention into the preset neural network, such that the neural network matches the semantic feature vector of the entity mention against semantic feature vectors of candidate entities in the candidate entity set and outputs the first matching result.

In some embodiments, generating the candidate entity set based on the feature comparison results between the entity mention and the entities in the knowledge graph includes: acquiring the feature comparison results by separately performing local character string-based feature comparison, pronunciation feature comparison, initial character feature comparison, and Dice similarity coefficient-based feature comparison on the entity mention and the entities in the knowledge graph; and placing entities with any one of following features in the feature comparison results into the candidate entity set: matching local character strings, consistent pronunciation, consistent initial characters, and a Dice similarity coefficient being greater than a coefficient threshold.

In some embodiments, prior to inputting the semantic feature vector of the entity mention into the preset neural network, the method further includes: screening the candidate entities in the candidate entity set.

In some embodiments, screening the candidate entities in the candidate entity set includes: screening the candidate entities in the candidate entity set in at least one of following screening fashions: coexistent keyword screening, synonym replacement-based coexistent keyword screening, and character length difference-based screening.

In some embodiments, the neural network is a Keras deep learning framework-based neural network.

In some embodiments, the knowledge graph is a medical knowledge graph.

According to a second aspect of the present disclosure, a knowledge graph-based question answering apparatus is provided. The apparatus includes a receiving module, a determining module, and an outputting module. The receiving module is configured to receive a query sentence. The determining module is configured to determine a target entity to which an entity mention in the query sentence is mapped in a knowledge graph. The outputting module is configured to output a result corresponding to the target entity in the knowledge graph.

In a possible implementation, the determining module is configured to: extract a semantic feature vector of the entity mention; and input the semantic feature vector of the entity mention into a preset neural network, such that the neural network matches the semantic feature vector of the entity mention against semantic feature vectors of entities in the knowledge graph and outputs a first matching result, wherein the first matching result is intended to indicate the target entity.

In a possible implementation, the determining module is configured to: acquire a second matching result by matching the entity mention against entities in the knowledge graph, wherein the second matching result includes a name of an entity matching the entity mention in the knowledge graph; and determine the entity indicated by the second matching result as the target entity.

In a possible implementation, the determining module is configured to: match the entity mention against entities in the knowledge graph; search the entity mention in a name dictionary in response to an absence of a second matching result, wherein the name dictionary includes a standard name and at least one alternative name of each entity, a name of a same entity in the knowledge graph is the same as a corresponding standard name, and the second matching result includes a name of an entity matching the entity mention in the knowledge graph; and determine an entity corresponding to an alternative name containing the entity mention as the target entity in response to a presence of the alternative name containing the entity mention in the name dictionary.

In a possible implementation, the determining module is configured to: match the entity mention against entities in the knowledge graph; search the entity mention in a name dictionary in response to an absence of a second matching result, wherein the name dictionary includes a standard name and at least one alternative name of each entity, a name of a same entity in the knowledge graph is the same as a corresponding standard name, and the second matching result includes a name of an entity matching the entity mention in the knowledge graph; and in response to an absence of an alternative name containing the entity mention in the name dictionary, extract a semantic feature vector of the entity mention, and input the semantic feature vector of the entity mention into a preset neural network, such that the neural network matches the semantic feature vector of the entity mention against semantic feature vectors of entities in the knowledge graph and outputs a first matching result, wherein the first matching result is intended to indicate the target entity.

In some embodiments, the determining module is configured to: generate a candidate entity set based on feature comparison results between the entity mention and the entities in the knowledge graph; and input the semantic feature vector of the entity mention into the preset neural network, such that the neural network matches the semantic feature vector of the entity mention against semantic feature vectors of candidate entities in the candidate entity set and outputs the first matching result.

In some embodiments, the determining module is configured to: acquire the feature comparison results by separately performing local character string-based feature comparison, pronunciation feature comparison, initial character feature comparison, and Dice similarity coefficient-based feature comparison on the entity mention and the entities in the knowledge graph; and place entities with any one of following features in the feature comparison results into the candidate entity set: matching local character strings, consistent pronunciation, consistent initial characters, and a Dice similarity coefficient being greater than a coefficient threshold.

In some embodiments, the apparatus further includes: a screening module, configured to screen the candidate entities in the candidate entity set.

In some embodiments, the screening module is configured to screen the candidate entities in the candidate entity set in at least one of following screening fashions: coexistent keyword screening, synonym replacement-based coexistent keyword screening, and character length difference-based screening.

In some embodiments, the receiving module is configured to receive the query sentence inputted according to a set sentence structure, wherein the set sentence structure is intended to determine a type of the entity mention.

According to a third aspect of the present disclosure, a computer device is provided. The computer device includes a memory, a processor, and at least one computer program stored in the memory and runnable on the processor. The processor, when running the computer program, is caused to implement the method provided in the first aspect of the present disclosure.

According to a fourth aspect of the present disclosure, a non-transitory computer-readable storage medium is provided. The computer-readable storage medium stores at least one computer program therein. The computer program, when run by a processor, causes the processor to implement the method provided in the first aspect of the present disclosure.

DETAILED DESCRIPTION

Figure 1:
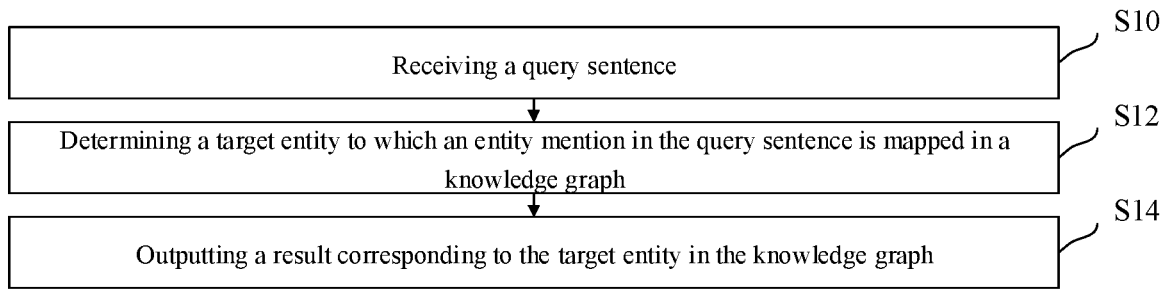
FIG. 1 is a schematic flowchart of a knowledge graph-based question answering method according to an embodiment of the present disclosure.

For clearer descriptions of the present disclosure, preferred embodiments are described in detail hereafter with reference to the accompanying drawings. The similar parts in the accompanying drawings are represented by similar reference numerals. A person skilled in the art should understand that the content described below in detail is illustrative and is not intended to limit the scope of protection of the present disclosure.

FIG. 1 is a schematic structural diagram of a knowledge graph-based question answering method according to an embodiment of the present disclosure. The method is performed by a terminal device or a server. As shown in FIG. 1, the method includes the following steps.

In S10, a query sentence is received.

In a possible implementation, when the method is performed by the terminal device, the terminal device receives the query sentence inputted by a user.

In embodiments of the present disclosure, a fashion of inputting the query sentence includes, but is not limited to, a text input fashion, a speech input fashion, and the like. In the text input fashion, an input box is displayed on an interaction interface, and the query sentence inputted by the user in a text form is received via the input box. In the speech input fashion, the query sentence inputted by the user in a speech form is received via a speech acquisition device (for example, a microphone, or the like).

In another possible implementation, when the method is performed by the server, the server receives the query sentence sent by the terminal device.

In S12, a target entity to which an entity mention in the query sentence is mapped in a knowledge graph is determined.

In S12, the entity mention in the query sentence is first recognized, and then the entity mention is linked to the target entity in the knowledge graph in a fashion of entity linking, thereby acquiring the target entity to which the entity mention is mapped in the knowledge graph.

In an example, the entity mention may be acquired by performing named entity recognition by using a conditional random field on the query sentence inputted by the user.

In S14, a result corresponding to the target entity in the knowledge graph is outputted.

For example, the knowledge graph includes a plurality of entities and association relationships between the entities. After the target entity is determined, other entities associated with the target entity may be acquired in a search fashion, and a found result is outputted.

In embodiments of the present disclosure, when the method is performed by the terminal device, a fashion of outputting the result corresponding to the target entity in the knowledge graph includes at least one of: a display fashion, a speech broadcast fashion, and the like.

For example, the display fashion includes a graphical display fashion and/or a text display fashion.

When the method is performed by the server, the fashion of outputting the result corresponding to the target entity in the knowledge graph includes: sending the result to the terminal device, such that the terminal device feeds back the result to the user in a display fashion, a speech broadcast fashion or the like.

In the embodiments of the present disclosure, the question answering method is implemented based on the knowledge graph. As the coverage of the knowledge graph is wide, the accuracy of the result corresponding to the target entity as searched is high by taking the knowledge graph as a knowledge base. In addition, the target entity is determined in the knowledge graph based on the entity mention in the query sentence, such that the target entity can be accurately determined, thereby further improving the accuracy of the result.

The knowledge graph is a research hotspot in the field of knowledge engineering at present. A medical knowledge graph is taken as an example. A medical knowledge graph technology may be used to connect various medical information to each other. The medical knowledge graph may be applied to intelligent medical applications such as question answering and auxiliary decision-making support. The knowledge graph-based question answering method provided in the embodiments of the present disclosure is exemplarily described by taking the field of medical question answering to which the medical knowledge graph is relatively widely applied as an example.

Figure 2:
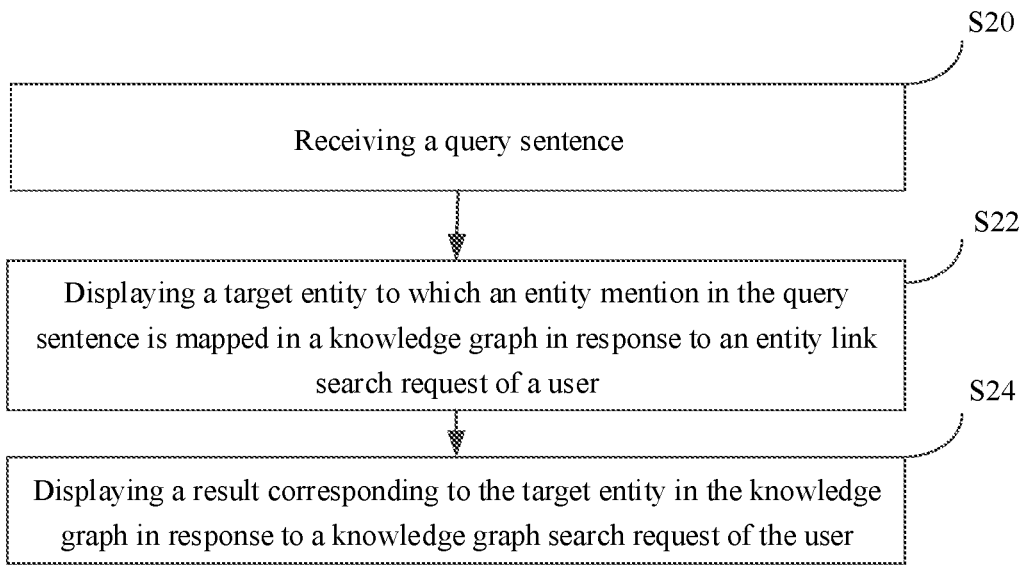
FIG. 2 is a schematic flowchart of a medical knowledge graph-based question answering method according to an embodiment of the present disclosure.

FIG. 2 is a schematic structural diagram of a medical knowledge graph-based question answering method according to an embodiment of the present disclosure. As shown in FIG. 2, the method includes the following steps.

In S20, a query sentence is received.

In a possible implementation, when the steps are performed by a terminal device, the query sentence inputted by a user may be received via a human-computer interaction component. The human-computer interaction component includes at least one of the following components: a microphone, a keyboard, a mouse, a touchscreen, and the like.

In another possible implementation, when the steps are performed by a server, the user inputs the query sentence on the terminal device. The terminal device sends the received query sentence to the server via a network. The server receives the query sentence sent by the terminal device.

Figure 3:
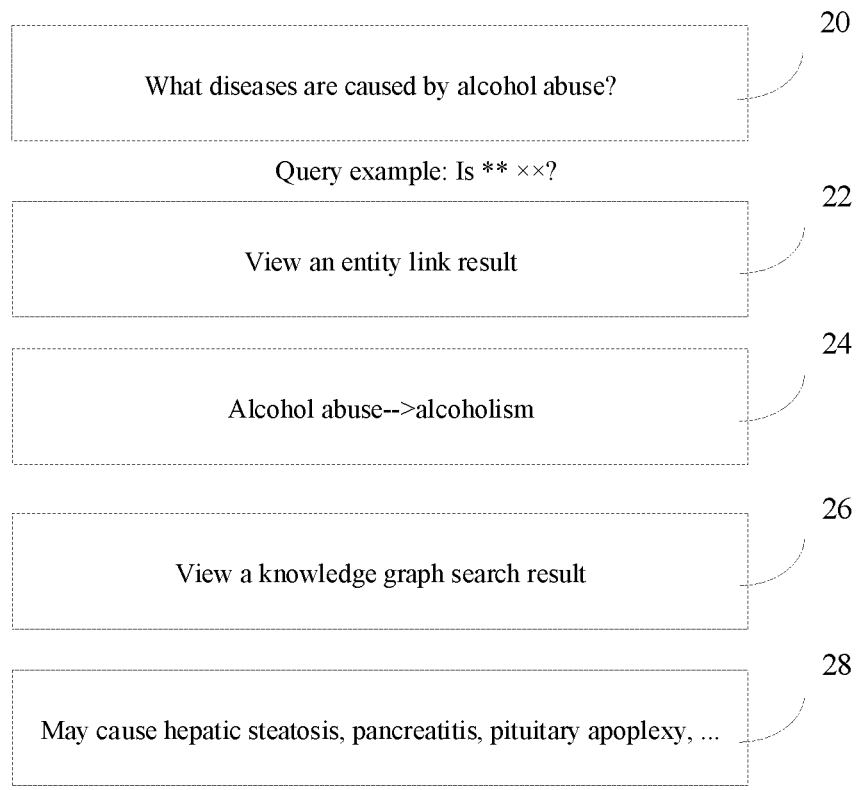
FIG. 3 is a schematic diagram of an interaction interface of a knowledge graph-based question answering system according to an embodiment of the present disclosure.
Figure 3:
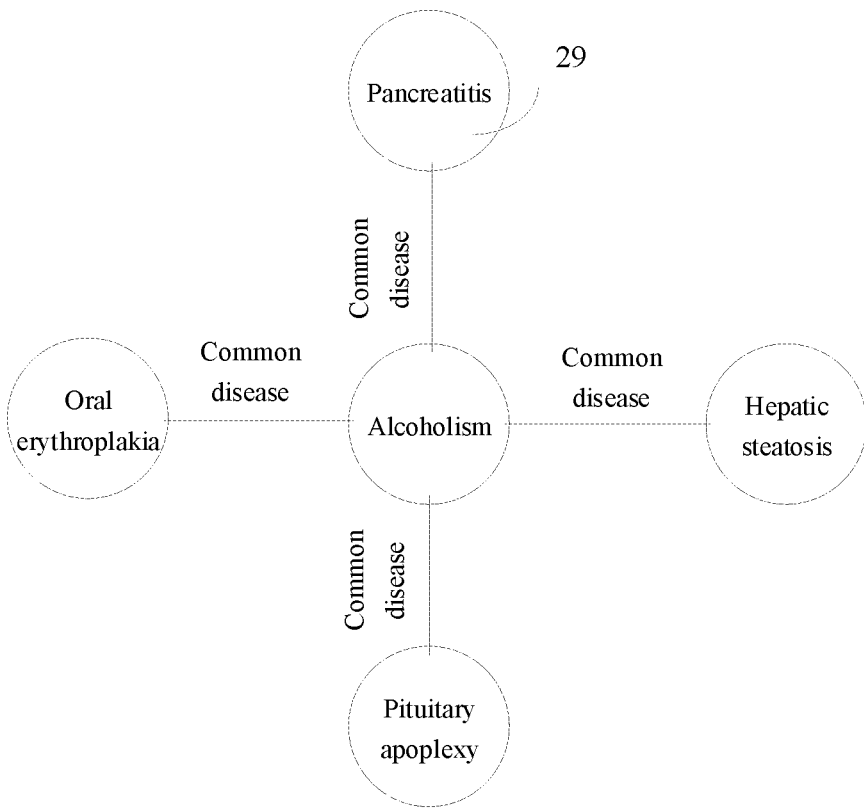

In an example, the terminal device presents an interaction interface in a visual form. As shown in FIG. 3, an input box 20 is displayed in an interaction interface. The user may input a query sentence, for example, "What diseases are caused by alcohol abuse?" into the input box.

In a possible implementation, S20 includes: receiving the query sentence inputted according to a set sentence structure, wherein the set sentence structure is intended to determine a type of the entity mention.

In an example, to enable the user to understand the set sentence structure, a query sentence example may be presented in the interaction interface. For example, a query sentence example such as "Is  xx?" is preset in the input box 20 or near (for example, below) the input box 20, wherein  may be a descriptor of a symptom, and xx may be a descriptor of a disease. In another example, the user is only allowed to input the descriptor of the symptom. For example, the user only needs to input "**" in the foregoing example but does not need to input "xx?" in the example. A system parses out that the entity mention in the query sentence is "alcohol abuse."

Certainly, a person skilled in the art can understand that an interaction input box in the present disclosure also supports that the user inputs a query sentence like "What are the symptoms of xx?" wherein xx represents a descriptor of a disease. For example, the query sentence is "What are the symptoms of high blood pressure?". In this example, the system parses out that the entity mention in the query sentence is "high blood pressure."

As can be seen, the type of the entity mention includes a symptom, a disease, or the like. The type of the entity mention can be distinguished by using the set sentence structure. In a knowledge graph, there are various entity types, and entities of the same name may exist in different entity types. The target entity can be determined more accurately by distinguishing the type of the entity mention.

In S22, a target entity to which an entity mention in the query sentence is mapped in a medical knowledge graph is displayed in response to an entity link search request of a user.

Next, the query sentence "What diseases are caused by alcohol abuse?" inputted by the user is still taken as an example to explain the present disclosure.

As shown in FIG. 3, the interaction interface further includes a search button, for example, a "View an entity link result" button 22. The user clicks the "View an entity link result" button 22 to initiate an entity link search request. The target entity (in the foregoing example of alcohol abuse, the target entity to which the entity mention is mapped is alcoholism) to which the entity mention (for example, alcohol abuse) is mapped in the medical knowledge graph is displayed in the interaction interface in response to the search request of the user (in response to that the user clicks the button 22 in the example in FIG. 3).

For example, the interaction interface is further provided with a display box 24. In the foregoing example, the entity mention and the target entity are displayed in the display box 24, for example, as shown in FIG. 3, alcohol abuse-->alcoholism. In this case, the user may clearly see what the entity mention and the target entity separately are. A person skilled in the art can understand that in other embodiments, the display box 24 may display only the target entity but does not display the entity mention.

It needs to be noted that, in other embodiments, after the query sentence is received, the target entity to which the entity mention in the query sentence is mapped in the medical knowledge graph may be automatically determined, and it is not necessary to wait for the user to send an entity link search request. In addition, in other embodiments, after the target entity is determined, S24 may be directly performed without displaying the target entity.

Figure 4:
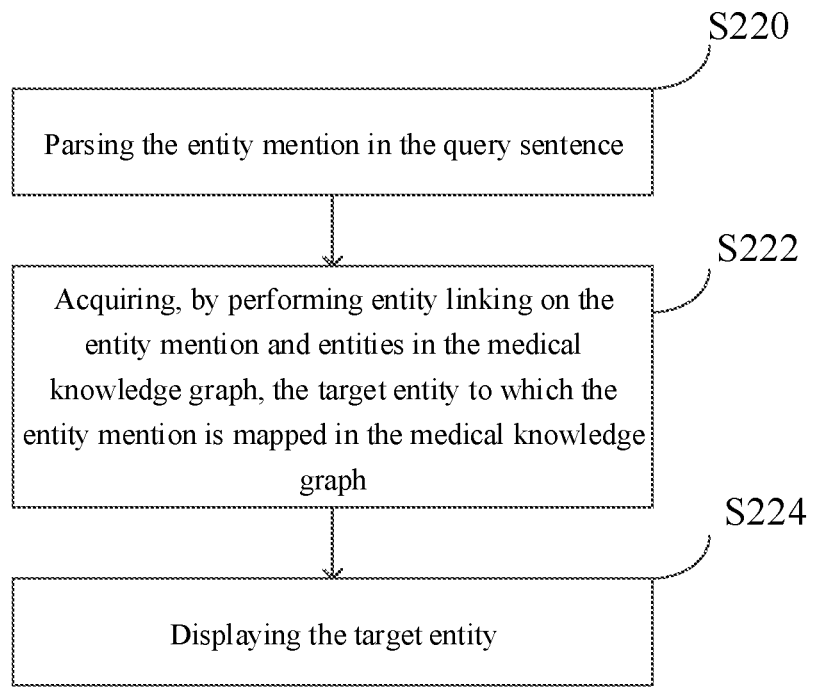
FIG. 4 is a flowchart of S22 in a knowledge graph-based question answering method according to an embodiment of the present disclosure.

As shown in FIG. 4, S22 further includes the following substeps.

In S220, the entity mention in the query sentence is parsed.

In an example, the entity mention may be acquired by performing the named entity recognition by using the conditional random field on the sentence inputted by the user.

In S222, the target entity to which the entity mention is mapped in the medical knowledge graph is acquired by performing entity linking on the entity mention and entities in the medical knowledge graph.

In an example, the medical knowledge graph in the embodiments contains a total of 14 entity types such as symptoms, prevention, the most common group of people, and the like. There are a total of over 70,000 entities and a total of over 200,000 triplets. For example, the triplets are in the form <entity, relationship, entity>.

In some optional implementations of the embodiments, S222 includes:

extracting a semantic feature vector of the entity mention; and inputting the semantic feature vector of the entity mention into a preset neural network, such that the neural network matches the semantic feature vector of the entity mention against semantic feature vectors of entities in the medical knowledge graph and outputs a first matching result, wherein the first matching result is intended to indicate the target entity.

In this implementation, the neural network is adopted to classify and determine the target entity corresponding to the entity mention accurately and efficiently, thereby ensuring the efficiency and accuracy of the entity linking, so as to ensure the response speed of question answering and the accuracy of answers.

Figure 5:
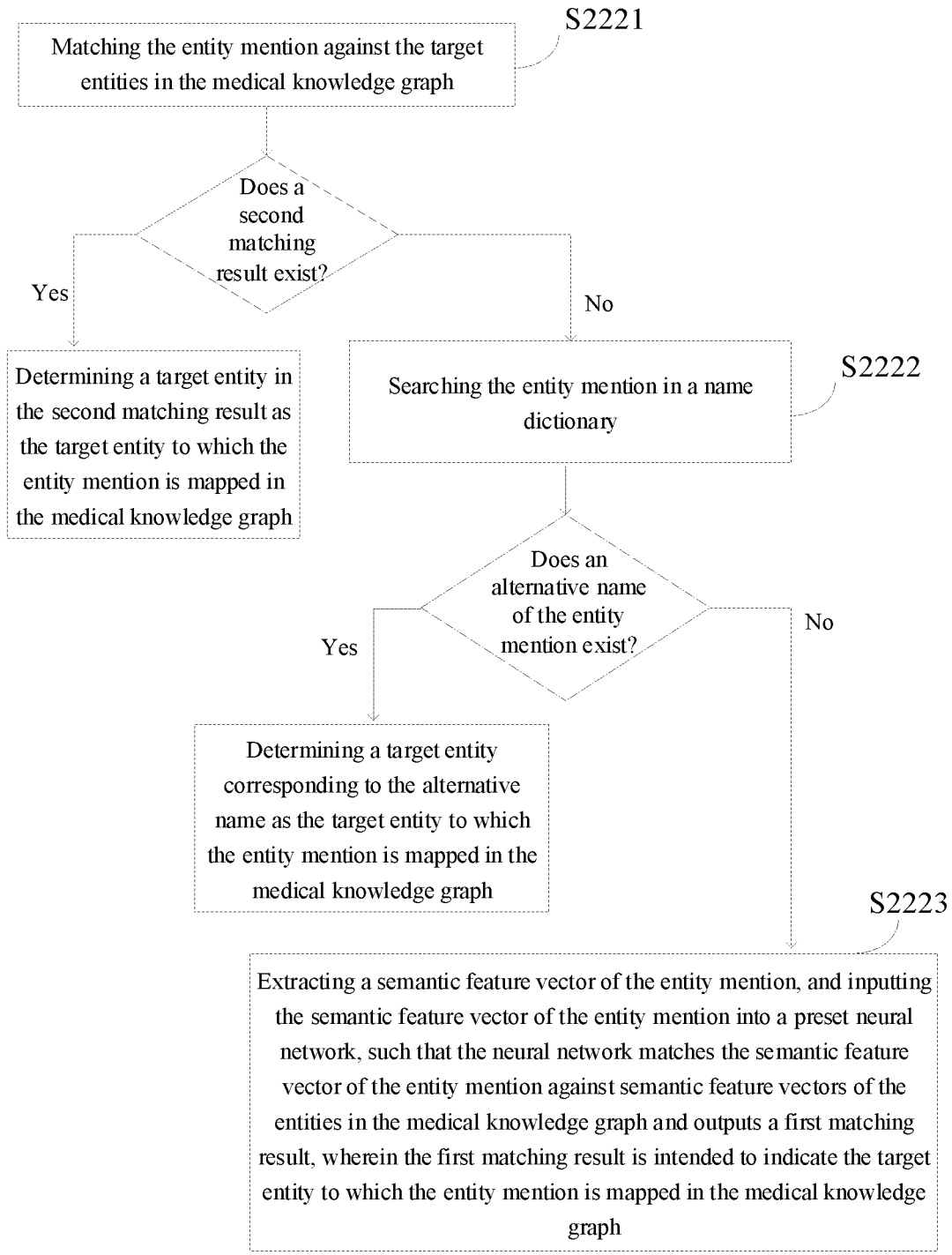
FIG. 5 is a flowchart of S222 in a knowledge graph-based question answering method according to an embodiment of the present disclosure.

In some other optional implementation of the embodiments, as shown in FIG. 5, S222 includes the following substeps.

In S2221, the entity mention is matched against entities in the medical knowledge graph, and if a second matching result (the second matching result includes the name of the entity matching the entity mention) exists, the entity indicated by the second matching result is taken as the target entity to which the entity mention is mapped in the medical knowledge graph.

In a specific example, matching the entity mention against the entities in the medical knowledge graph includes: if a name of an entity in the medical knowledge graph is the same as characters of the entity mention, determining that the name of the entity precisely matches the entity mention, so as to acquire a second matching result.

If a second matching result does not exist, S2222 is performed.

In S2222, the entity mention is searched in a name dictionary, wherein the name dictionary includes a standard name and at least one alternative name of each entity, and a name of the same entity in the knowledge graph is the same as a corresponding standard name.

If an alternative name of the entity mention exists in the name dictionary, an entity corresponding to the alternative name is taken as the target entity to which the entity mention is mapped in the medical knowledge graph. Herein, a standard name of an entity is a name of the entity in the medical knowledge graph.

In a specific example, a key value of the name dictionary is a title name in Baidu Baike, and a value is a name in an alternative name tag. If the entity mention is contained in a value, a corresponding key value is returned as the target entity to which the entity mention is mapped in the medical knowledge graph.

If the alternative name of the entity mention does not exist in the name dictionary, S2223 is performed.

In S2223, a semantic feature vector of the entity mention is extracted, and the semantic feature vector of the entity mention is inputted into a preset neural network, such that the neural network matches the semantic feature vector of the entity mention against semantic feature vectors of entities in the medical knowledge graph and outputs a first matching result, wherein the first matching result is intended to indicate the target entity.

In some optional implementations of the embodiments, the neural network is based on Keras deep learning framework.

In some optional implementations of the embodiments, S2223 includes the following steps.

In the first step, a candidate entity set is generated based on feature comparison results between the entity mention and the entities in the medical knowledge graph.

In some optional implementations of the embodiments, the first step includes:

acquiring the feature comparison results by separately performing local character string-based feature comparison, pronunciation feature comparison, initial character feature comparison, and Dice similarity coefficient-based feature comparison on the entity mention and the entities in the medical knowledge graph; and placing entities with any one of following features in the feature comparison results into the candidate entity set: matching local character strings, consistent pronunciation, consistent initial characters, and a Dice similarity coefficient being greater than a coefficient threshold.

This implementation is based on the comparison of various features. The accuracy and recall of the candidate entity set can be ensured, and meanwhile, the efficiency of entity linking is improved, thereby improving the response speed of question answering at the same time when the accuracy of answers is ensured. Specifically, feature comparison results of four types, that is, matching local character strings, consistent pronunciation, consistent initial characters, and a Dice similarity coefficient being greater than a coefficient threshold are set according to characteristics of Chinese text.

The matching local character strings are any one of the cases that an entity mention is contained in an entity, an entity mention contains an entity, a single character in a character string of an entity mention is contained in a character string of an entity.

The consistent pronunciation means that the pronunciation of an entity mention is the same as the pronunciation of a name of a candidate entity. If the pronunciation of an entity mention is the same as the pronunciation of a name of a candidate entity, for an entity mention with a spelling error, a corresponding candidate entity can still be found, which helps to increase the recall of the candidate entity set.

The consistent initial characters mean that the first character in a character string of an entity mention is the same as the first character in a character string of a candidate entity.

The Dice similarity coefficient is used for measuring similarity between a character string of an entity mention and a character string of a candidate entity. If the Dice similarity coefficient is greater than the coefficient threshold, the entity is the candidate entity. In comparison, if the Dice similarity coefficient is not greater than the coefficient threshold, the entity is not the candidate entity.

In the second step, a semantic feature vector of the entity mention is extracted, and the semantic feature vector of the entity mention is inputted into the preset neural network, such that the neural network matches the semantic feature vector of the entity mention against the semantic feature vectors of candidate entities in the candidate entity set and outputs a first matching result, wherein the first matching result is intended to indicate the target entity.

This implementation can improve the efficiency of entity linking, thereby improving the response speed of question answering.

In some examples, to avoid the operation of manually designing features, a feature vector containing semantic information is acquired by extracting the semantic feature vector of the entity mention and the semantic feature vector of the candidate entity directly using word2vec. The semantic feature vector is inputted into the Keras deep learning framework-based neural network, such that the neural network accurately determines the target entity by classifying <entity mention, candidate entity>. Network parameters of the Keras deep learning framework-based neural network for implementing binary classification may be set as follows: the input dimension is a semantic vector value of 400, epochs are set to 50, batch_size is set to 512, relu is used as a fully-connected network of an activation function, and binary_crossentropy is used as a loss function. The experiment shows that the accuracy of classifying the neural network may be up to 95% or higher.

In the embodiments of the present disclosure, the Keras deep learning framework-based neural network outputs a probability value that the candidate entity in <entity mention, candidate entity> is a target entity, and the target entity is a candidate entity corresponding to a maximum probability value.

This optional fashion is set based on factors such as comprehensive execution efficiency and effectiveness and includes a plurality of fashions for implementing entity linking that are executed in sequence. The efficiency of entity linking can be further improved meanwhile the accuracy of entity linking is ensured, thereby further improving the response speed of question answering meanwhile the accuracy of answers is ensured.

In some optional implementations of the embodiments, prior to the second step, S2223 further includes: screening the candidate entities in the candidate entity set.

A number of the candidate entities in the candidate entity set can be reduced by screening the candidate entities in the candidate entity set, so as to improve the efficiency of entity linking, thereby improving the response speed of question answering.

In some optional implementations of the embodiments, screening the candidate entities in the candidate entity set includes: performing at least one of coexistent keyword screening, synonym replacement-based coexistent keyword screening, and character length difference-based screening on the candidate entities in the candidate entity set.

In the coexistent keyword screening, if a keyword such as a body part is included in both an entity mention and a candidate entity, the corresponding candidate entity is kept. If a keyword is not included in both an entity mention and a candidate entity, the corresponding candidate entity is deleted.

In the synonym replacement-based coexistent keyword screening, synonym replacement is performed on a keyword in an entity mention, and coexistent keyword screening is performed on the entity mention after replacement and candidate entities; alternatively, synonym replacement is performed on keywords in candidate entities, and coexistent keyword screening is performed on an entity mention and the candidate entities after replacement.

For example, excrement and feces are synonyms. After synonym replacement is performed on a keyword in an entity mention or a candidate entity, if the keyword exists in both the entity mention and the candidate entity after replacement, the corresponding candidate entity is kept. If the keyword does not exist in both the entity mention and the candidate entity after replacement, the candidate entity is screened out.

In character length difference-based screening, if a character length difference between an entity mention and a candidate entity does not exceed a threshold, the corresponding candidate entity is kept. If a character length difference between an entity mention and a candidate entity exceeds the threshold, the corresponding candidate entity is deleted. For example, the threshold is 4.

This implementation is based on multi-dimensional screening, the accuracy and recall of the candidate entity set can be ensured, and meanwhile, the efficiency of entity linking can be improved, thereby further increasing the response speed of question answering meanwhile the accuracy of answers is ensured.

The foregoing S2221 to S2223 are set based on factors such as comprehensive execution efficiency and effectiveness and include a plurality of fashions for implementing entity linking that are executed in sequence. The efficiency of entity linking can be further improved meanwhile the accuracy of entity linking is ensured, thereby further improving the response speed of question answering meanwhile the accuracy of answers is ensured.

It needs to be noted that the execution order of the foregoing steps in the embodiments of the present disclosure is not limited as long as a target entity can be determined and a result of the target entity in the knowledge graph can be determined.

Specifically, this is an entity linking method designed according to characteristics of Chinese text in the medical field, and the method is applied to medical question answering. Based on that the medical knowledge graph is used as a knowledge base and an entity mention is acquired by performing named entity recognition, precise matching is performed first. If a target entity fails to be matched in the medical knowledge graph through precise matching, the entity mention is then searched in the name dictionary. If a target entity also fails to be found through the search in the name dictionary, a high-quality candidate entity set constructed based on a plurality of features is finally used. During disambiguation of candidate entities, the accuracy of linking an entity to a target entity is improved by using a neural network and a feature vector (word vector) containing semantic information, thereby increasing the accuracy of answers.

The method provided in the embodiments is used in a Chinese medical corpus to perform entity linking, and an entity mention can be accurately mapped to a target entity in the medical knowledge graph, such that a Cypher sentence in neo4j may be used to search the medical knowledge graph, and an acquired result is outputted as an answer, thereby achieving advantages such as fast response and high accuracy and providing practical value.

In a possible implementation, if at least two target entities are determined from the medical knowledge graph by using the foregoing S2221 to S2223 and the at least two target entities correspond to different entity types, in a case that a query sentence is inputted in a set sentence structure, the method further includes: determining a type of the target entity according to the set sentence structure; and selecting a unique target entity by using the type of the target entity.

After S222, S22 further includes:

In S224, a name of the target entity is displayed.

For example, the name of the target entity is displayed in the display box 24.

After S22, the question answering method in the embodiments of the present disclosure further includes the following step.

In S24, a result corresponding to the target entity in the knowledge graph is displayed in response to a knowledge graph search request.

As shown in FIG. 3, a search button, for example, a "View a knowledge graph search result" button 26 is further displayed in the foregoing interaction interface. A result corresponding to the target entity in the knowledge graph is displayed in response to a search request of the user (in response to that the user clicks the button 26 in the example in FIG. 3).

For example, in an example in which the target entity is alcoholism, diseases related to alcoholism are displayed. In an example in which the target entity is high blood pressure, symptoms corresponding to high blood pressure are displayed.

In the example as shown in FIG. 3, a result is displayed in a display box 28 in a text form (for example, a sentence fashion). In the foregoing example of alcohol abuse, "may cause hepatic steatosis, pancreatitis, pituitary apoplexy, . . . " is displayed in the display box 28. When the sentence is relatively long and exceeds a display boundary of the display box 28, the part that is not shown is replaced by ". . . ." When the user needs to view ". . .," the user may float a cursor of a pointer device such as a mouse on the display box 28. In this case, the complete sentence is displayed floating.

In another example, the result is displayed in the form of a displayed topological graph 29 as shown in FIG. 3, thereby displaying the result in a more intuitive graphical fashion. In the foregoing example of alcohol abuse, in the displayed topological graph 29, with the target entity (alcoholism) as the center, corresponding query results such as hepatic steatosis, pancreatitis, and pituitary apoplexy are presented in a radiation form. The diseases are connected to alcoholism by arrows.

A person skilled in the art can understand that the graph is not limited to the topological graph, and for example, may further be a tree relationship diagram.

In still another example, the result may be presented in a text fashion and a graphical fashion at the same time.

It needs to be noted that, in other embodiments, after S22, the result corresponding to the target entity in the knowledge graph may be further directly displayed, and the knowledge graph search request does not need to be used as a trigger condition.

In the question answering method provided in the embodiments, a sentence that is inputted by the user and may contain an abbreviation, an acronym, an irregular expression, or a vague expression is accurately mapped to the target entity in the medical knowledge graph by using entity linking, such that an answer can be accurately found, thereby achieving advantages such as fast response and relatively high accuracy.

A person skilled in the art may understand that the foregoing examples are a medical knowledge graph-based system and method. However, the question answering method provided in the foregoing embodiments may also be applied to question answering systems in other fields as well as fields such as knowledge graph-based intelligent search and personalized recommendation.

The medical knowledge graph-based question answering method provided in the foregoing embodiments may be implemented by the terminal device. The terminal device may be one of various electronic devices that include, but are not limited to, a personal computer, a smartphone, a tablet computer, a personal digital assist, and the like.

In addition, the medical knowledge graph-based question answering method provided in the foregoing embodiments may further be implemented by a server. The terminal device receives the query sentence inputted by the user and sends the query sentence to the server. The server may be a server that provides various services. The server may perform processing such as storage and analysis on received data (the query sentence that is inputted by the user and is sent by the terminal device), and feedback a processing result (a question answering result) to the terminal device. The terminal device outputs the processing result to the user by using an interaction module such as a touchscreen. The terminal device communicates with the server via a network. The network may include a network of one of various types such as a wired communication link, a wireless communication link, a fiber-optic cable.

In the embodiments, a specific implementation of the so-called "receive" corresponds to a fashion of using the terminal device by the user. For example, the user inputs data into a personal computer by a keyboard. The personal computer receives the data inputted by the user. For example, the user inputs the data in a fashion such as mouse clicks and keyboard operations on a GUI of an application based on the medical knowledge graph-based question answering method on the personal computer. The personal computer captures these operations to receive the data inputted by the user. For example, the user inputs the data in a speech fashion. The personal computer uses a speech-to-text method to receive the data inputted by the user. For example, the user uses a mobile phone application (App), and the server may interact with a mobile phone used by the user to receive the data inputted by the user.

Figure 6:
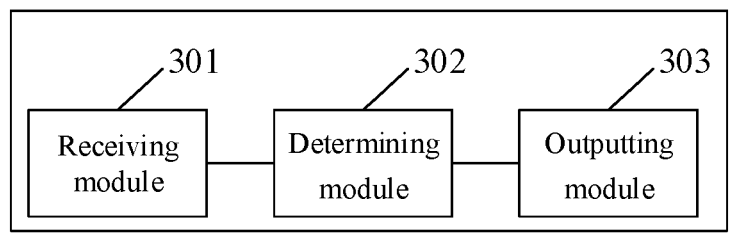
FIG. 6 is a schematic structural diagram of a knowledge graph-based question answering apparatus according to an embodiment of the present disclosure.

FIG. 6 is a schematic structural diagram of a knowledge graph-based question answering apparatus according to an embodiment of the present disclosure. As shown in FIG. 6, the apparatus includes a receiving module 301, a determining module 302, and an outputting module 303. The receiving module 301 is configured to receive a query sentence. The determining module 302 is configured to determine a target entity to which an entity mention in the query sentence is mapped in a knowledge graph. The outputting module 303 is configured to output a result corresponding to the target entity in the knowledge graph.

In a possible implementation, the determining module 302 is configured to: extract a semantic feature vector of the entity mention; and input the semantic feature vector of the entity mention into a preset neural network, such that the neural network matches the semantic feature vector of the entity mention against semantic feature vectors of entities in the knowledge graph and outputs a first matching result, wherein the first matching result is intended to indicate the target entity.

In a possible implementation, the determining module 302 is configured to: acquire a second matching result by matching the entity mention against entities in the knowledge graph, wherein the second matching result includes a name of an entity matching the entity mention in the knowledge graph; and determine the entity indicated by the second matching result as the target entity.

In a possible implementation, the determining module 302 is configured to: match the entity mention against entities in the knowledge graph; search the entity mention in a name dictionary in response to an absence of a second matching result, wherein the name dictionary includes a standard name and at least one alternative name of each entity, a name of a same entity in the knowledge graph is the same as a corresponding standard name, and the second matching result includes a name of an entity matching the entity mention in the knowledge graph; and determine an entity corresponding to an alternative name containing the entity mention as the target entity in response to a presence of the alternative name containing the entity mention in the name dictionary.

In a possible implementation, the determining module 302 is configured to: match the entity mention against entities in the knowledge graph; search the entity mention in a name dictionary in response to an absence of a second matching result, wherein the name dictionary includes a standard name and at least one alternative name of each entity, a name of a same entity in the knowledge graph is the same as a corresponding standard name, and the second matching result includes a name of an entity matching the entity mention in the knowledge graph; and in response to an absence of an alternative name containing the entity mention in the name dictionary, extract a semantic feature vector of the entity mention, and input the semantic feature vector of the entity mention into a preset neural network, such that the neural network matches the semantic feature vector of the entity mention against semantic feature vectors of entities in the knowledge graph and outputs a first matching result, wherein the first matching result is intended to indicate the target entity.

In some embodiments, the determining module 302 is configured to: generate a candidate entity set based on feature comparison results between the entity mention and the entities in the knowledge graph; and input the semantic feature vector of the entity mention into the preset neural network, such that the neural network matches the semantic feature vector of the entity mention against semantic feature vectors of candidate entities in the candidate entity set and outputs the first matching result.

In some embodiments, the determining module 302 is configured to: acquire the feature comparison results by separately performing local character string-based feature comparison, pronunciation feature comparison, initial character feature comparison, and Dice similarity coefficient-based feature comparison on the entity mention and the entities in the knowledge graph; and place entities with any one of following features in the feature comparison results into the candidate entity set: matching local character strings, consistent pronunciation, consistent initial characters, and a Dice similarity coefficient being greater than a coefficient threshold.

In some embodiments, the apparatus further includes: a screening module, configured to screen the candidate entities in the candidate entity set.

In some embodiments, the screening module is configured to screen the candidate entities in the candidate entity set in at least one of following screening fashions: coexistent keyword screening, synonym replacement-based coexistent keyword screening, and character length difference-based screening.

In some embodiments, the receiving module 301 is configured to receive the query sentence inputted according to a set sentence structure, wherein the set sentence structure is intended to determine a type of the entity mention.

In an example, the knowledge graph-based question answering apparatus provided in the foregoing embodiments are implemented by a personal computer. The personal computer stores human-computer interaction software. A question answering system module developed by using python is encapsulated and then invoked in software. A user may view a graphical search result. The interaction interface is as shown in FIG. 3.

It needs to be noted that for the knowledge graph-based question answering apparatus provided in the foregoing embodiments, during question answering, the division of the foregoing functional modules is only an example for description. During actual application, the foregoing functions may be allocated to different functional modules as required. That is, the internal structure of the apparatus is divided into different functional modules, to complete all or some functions described above. In addition, the knowledge graph-based question answering apparatus provided in the foregoing embodiments and the embodiments of the knowledge graph-based question answering method belong to the same concept. For a specific implementation process of the knowledge graph-based question answering apparatus, reference may be made to the method embodiments. Details are not described herein again.

Figure 7:
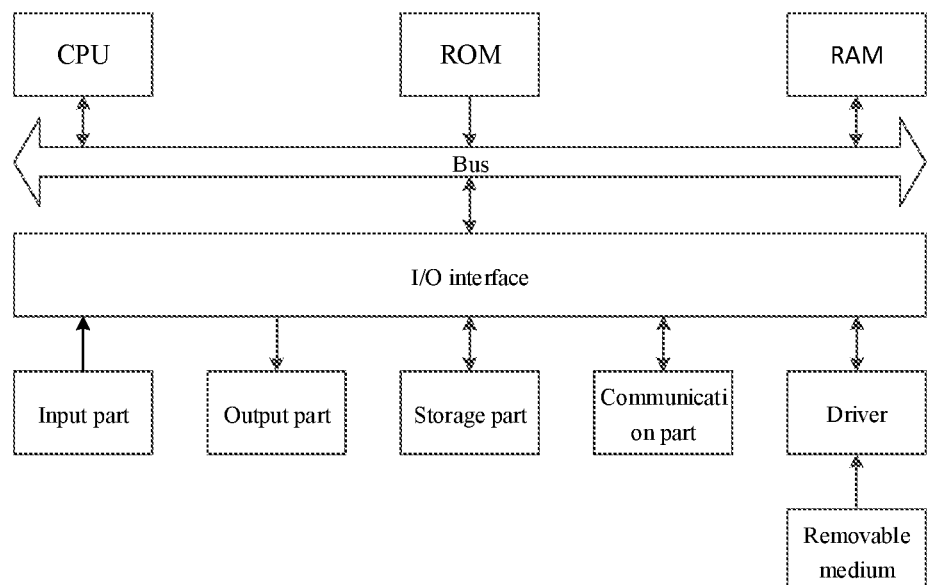
FIG. 7 is a schematic structural diagram of a computer device for implementing a knowledge graph-based question answering method according to an embodiment of the present disclosure.

As shown in FIG. 7, a computer device suitable for implementing a medical knowledge graph-based question answering system provided in the foregoing embodiments includes a central processing unit (CPU) may perform various appropriate actions and processing according to a program stored in a read-only memory (ROM) or a program loaded into a random access memory (RAM) from a storage part. The RAM further stores various programs and data required for the operation of a computer system. The CPU, the ROM, and the RAM are connected by a bus. An input/output (I/O) interface is also connected to the bus.

The following parts that are connected to the I/O interface include an input part such as a keyboard, a mouse, and the like, an output part such as a liquid crystal display (LCD), a speaker, and the like, a storage part such as a hard disk, and the like, and a communication part of a network interface card such as a LAN card, a modem, and the like. The communication part performs communication via a network such as the Internet. A driver is also connected to the I/O interface as required. A removable medium such as a magnetic disk, an optical disc, a magneto-optical disc, a semiconductor memory, or the like is installed on the driver as required, such that a computer program read from the driver is installed in the storage part as required.

Especially, according to the embodiments, the process described in the foregoing flowcharts may be implemented as a computer software program. For example, the embodiments include a computer program product, including a computer program tangibly contained in a computer-readable medium. The computer program contains program code used for performing the method as shown in the flowcharts. In the embodiments, the computer program may be downloaded and installed from a network through the communication part and/or installed from the removable medium.

The flowcharts and schematic diagrams in the accompanying drawings show the possible architecture, functions, and operations of the system of the method and the computer program product according to the embodiments. In this regard, each block in the flowcharts or schematic diagrams can represent a part of a module, a program segment, or a code, and the part of the module, the program segment, or the code contains one or more executable instructions for implementing the defined logical functions. It should also be noted that in some implementations as alternatives, the functions labeled in the blocks can occur in an order different from the order labeled in the accompanying drawings. For example, two sequentially shown blocks can be substantially executed in parallel in fact, and they sometimes can also be executed in a reverse order, which is defined by the referred functions. It should also be noted that each block in the schematic diagrams and/or the flowcharts and the combination of the blocks in the schematic diagrams and/or the flowcharts can be implemented by a dedicated system based on hardware for executing the defined functions or operations, or can be implemented by a combination of the dedicated hardware and computer instructions.

The modules described in the embodiments may be implemented in a software fashion or may be implemented in a hardware fashion. The described modules may also be disposed in a processor, for example, may be described as a processor, including a receiving module, a determining module, and the like. The names of these modules do not constitute a limitation to the modules in some cases.

In another aspect, the embodiments further provide a non-transitory computer storage medium. The non-transitory computer storage medium may be a non-transitory computer storage medium contained in the foregoing apparatus in the foregoing embodiment or may be a non-transitory computer storage medium that exists separately and is not assembled in a terminal. The non-transitory computer storage medium stores one or more programs therein. The one or more programs, when running on a device, causes the device to implement the foregoing method.

It should be noted that the terms "include," "comprise," or any variation thereof in the description of the present disclosure are intended to cover a non-exclusive inclusion. Therefore, in the context of a process, a method, an object, or a device that includes a series of elements, the process, method, object, or device not only includes such elements, but also includes other elements not specified expressly, or may include inherent elements of the process, method, object or device. If no more limitations are made, an element limited by "include a/an . . . " does not exclude other same elements existing in the process, method, object, or device which includes the element.

The foregoing embodiments of the present disclosure are merely examples for the clear description of the present disclosure, rather than a limitation to implementations of the present disclosure. For a person of ordinary skill in the art, other changes or variations in different forms may also be made based on the foregoing description. All implementations cannot be exhaustively listed herein. Obvious changes or variations that are derived from the technical solutions of the present disclosure still fall within the scope of protection of the present disclosure.

What is claimed is:

1. A knowledge graph-based question answering method, comprising:
    receiving a query sentence;
    matching entity mention in the query sentence against entities in a knowledge graph;
    searching the entity mention in a name dictionary in response to an absence of a second matching result, wherein the second matching result comprises a name of an entity matching the entity mention in the knowledge graph, and the name dictionary comprises a standard name and at least one alternative name of each entity, a name of a same entity in the knowledge graph is the same as a corresponding standard name;
    extracting a semantic feature vector of the entity mention in response to an absence of the alternative name containing the entity mention in the name dictionary, and inputting the semantic feature vector of the entity mention into a preset neural network, such that the neural network matches the semantic feature vector of the entity mention against semantic feature vectors of entities in the knowledge graph and outputs a first matching result, wherein the first matching result is intended to indicate a target entity to which the entity mention is mapped in the knowledge graph; and
    outputting a result corresponding to the target entity in the knowledge graph.

2. The method according to claim 1, wherein the method further comprises:
   determining the entity indicated by the second matching result as the target entity in response to a presence of the second matching result.

3. The method according to claim 1, wherein the method further comprises:
   determining an entity corresponding to an alternative name containing the entity mention as the target entity in response to a presence of the alternative name containing the entity mention in the name dictionary.

4. The method according to claim 1, wherein inputting the semantic feature vector of the entity mention into the preset neural network, such that the neural network matches the semantic feature vector of the entity mention against the semantic feature vectors of the entities in the knowledge graph and outputs the first matching result comprises:
   generating a candidate entity set based on feature comparison results between the entity mention and the entities in the knowledge graph; and
   inputting the semantic feature vector of the entity mention into the preset neural network, such that the neural network matches the semantic feature vector of the entity mention against semantic feature vectors of candidate entities in the candidate entity set and outputs the first matching result.

5. The method according to claim 4, wherein generating the candidate entity set based on the feature comparison results between the entity mention and the entities in the knowledge graph comprises:
   acquiring the feature comparison results by separately performing local character string-based feature comparison, pronunciation feature comparison, initial character feature comparison, and Dice similarity coefficient-based feature comparison on the entity mention and the entities in the knowledge graph; and
   placing entities with any one of following features in the feature comparison results into the candidate entity set: matching local character strings, consistent pronunciation, consistent initial characters, and a Dice similarity coefficient being greater than a coefficient threshold.

6. The method according to claim 5, wherein prior to inputting the semantic feature vector of the entity mention into the preset neural network, the method further comprises:
   screening the candidate entities in the candidate entity set.

7. The method according to claim 6, wherein screening the candidate entities in the candidate entity set comprises:
   screening the candidate entities in the candidate entity set in at least one of following screening fashions: coexistent keyword screening, synonym replacement-based coexistent keyword screening, and character length difference-based screening.

8. The method according to claim 1, wherein the neural network is a Keras deep learning framework-based neural network.

9. The method according to claim 1, wherein receiving the query sentence comprises:
   receiving the query sentence inputted according to a set sentence structure, wherein the set sentence structure is intended to determine a type of the entity mention.

10. The method according to claim 1, wherein the knowledge graph is a medical knowledge graph.

11. A computer device, comprising a memory, a processor, and at least one computer program stored in the memory and runnable on the processor, wherein the processor, when running the computer program, is caused to perform:
   receiving a query sentence;
   matching entity mention in the query sentence against entities in a knowledge graph;
   searching the entity mention in a name dictionary in response to an absence of a second matching result, wherein the second matching result comprises a name of an entity matching the entity mention in the knowledge graph, and the name dictionary comprises a standard name and at least one alternative name of each entity, a name of a same entity in the knowledge graph is the same as a corresponding standard name;
   extracting a semantic feature vector of the entity mention in response to an absence of the alternative name containing the entity mention in the name dictionary, and inputting the semantic feature vector of the entity mention into a preset neural network, such that the neural network matches the semantic feature vector of the entity mention against semantic feature vectors of entities in the knowledge graph and outputs a first matching result, wherein the first matching result is intended to indicate a target entity to which the entity mention is mapped in the knowledge graph; and
   outputting a result corresponding to the target entity in the knowledge graph.

12. A non-transitory computer-readable storage medium, storing at least one computer program therein, wherein the computer program, when run by a processor, causes the processor to perform:
   receiving a query sentence;
   matching entity mention in the query sentence against entities in a knowledge graph;
   searching the entity mention in a name dictionary in response to an absence of a second matching result, wherein the second matching result comprises a name of an entity matching the entity mention in the knowledge graph, and the name dictionary comprises a standard name and at least one alternative name of each entity, a name of a same entity in the knowledge graph is the same as a corresponding standard name;
   extracting a semantic feature vector of the entity mention in response to an absence of the alternative name containing the entity mention in the name dictionary, and inputting the semantic feature vector of the entity mention into a preset neural network, such that the neural network matches the semantic feature vector of the entity mention against semantic feature vectors of entities in the knowledge graph and outputs a first matching result, wherein the first matching result is intended to indicate a target entity to which the entity mention is mapped in the knowledge graph; and
   outputting a result corresponding to the target entity in the knowledge graph.

13. The computer device according to claim 11, wherein the processor, when running the computer program, is caused to perform:
   determining the entity indicated by the second matching result as the target entity in response to a presence of the second matching result.

14. The computer device according to claim 11, wherein the processor, when running the computer program, is caused to perform:
   determining an entity corresponding to an alternative name containing the entity mention as the target entity in response to a presence of the alternative name containing the entity mention in the name dictionary.

15. The computer device according to claim 11, wherein the processor, when running the computer program, is caused to perform:
  generating a candidate entity set based on feature comparison results between the entity mention and the entities in the knowledge graph; and
  inputting the semantic feature vector of the entity mention into the preset neural network, such that the neural network matches the semantic feature vector of the entity mention against semantic feature vectors of candidate entities in the candidate entity set and outputs the first matching result.

16. The computer device according to claim 15, wherein the processor, when running the computer program, is caused to perform:
  acquiring the feature comparison results by separately performing local character string-based feature comparison, pronunciation feature comparison, initial character feature comparison, and Dice similarity coefficient-based feature comparison on the entity mention and the entities in the knowledge graph; and
  placing entities with any one of following features in the feature comparison results into the candidate entity set: matching local character strings, consistent pronunciation, consistent initial characters, and a Dice similarity coefficient being greater than a coefficient threshold.

* * * * *